United States Patent
Birmingham

[11] Patent Number: 5,877,366
[45] Date of Patent: Mar. 2, 1999

[54] DICYCLOPENTADIENE CRACKING PROCESS

[75] Inventor: John M. Birmingham, Platteville, Colo.

[73] Assignee: Boulder Scientific Company, Mead, Colo.

[21] Appl. No.: 861,332

[22] Filed: Mar. 25, 1992

Related U.S. Application Data

[63] Continuation of Ser. No. 569,657, Aug. 20, 1990, abandoned.

[51] Int. Cl.⁶ .................................................. C07C 4/22
[52] U.S. Cl. ............................................ 585/354; 585/832
[58] Field of Search ..................................... 585/354, 832

[56] References Cited

U.S. PATENT DOCUMENTS

| | | | |
|---|---|---|---|
| 2,453,044 | 11/1948 | Staff | 585/354 |
| 2,831,904 | 4/1958 | Kreps | 585/354 |
| 3,544,644 | 12/1970 | Robota | 585/354 |
| 3,590,089 | 6/1971 | Robota | 585/354 |

FOREIGN PATENT DOCUMENTS

| | | |
|---|---|---|
| 0457038 | 5/1949 | Canada. |
| 6059719 | 5/1981 | Japan. |

*Primary Examiner*—Walter D. Griffin
*Attorney, Agent, or Firm*—Edward S. Irons

[57] ABSTRACT

A process and a system for cracking dicyclopentadiene are disclosed pursuant to the process preheated dicyclopentadiene is introduced into a heated transfer fluid sufficiently below the transfer fluid surface to accomplish substantially complete conversion of said dicyclopentadiene to monomeric cyclopentadiene vapor.

3 Claims, 1 Drawing Sheet

DICYCLOPENTADIENE CRACKING PROCESS

This is a continuation of application Ser. No. 07/569,657, filed Aug. 20, 1990, now abandoned.

This invention relates to the thermal decomposition of dicyclopentadiene, $C_{10}H_{12}$, to produce cyclopentadiene monomer, $C_5H_6$.

BACKGROUND OF THE INVENTION

Various dicyclopentadiene cracking methods are known. The dissociation to the monomer is a monomolecular reaction. The cracking can be accomplished by distilling dicyclopentadiene under atmospheric pressure. Dicyclopentadiene boils at 170° C. It cracks at a rate of 36% per hour at 170° C. Monomer is obtained by maintaining the top temperature of the fractionating column at 41°–42° C.

Another procedure involves adding dicyclopentadiene to a hot liquid, e.g., a high boiling oil at 250°–260° C. The resulting vapors are fractionated to remove refluxing uncracked dimer and entrained liquid. A commercial procedure entails vapor phase cracking at 350°–400° C. See, generally, "Cyclopentadiene and Dicyclopentadiene", Kirk-Othmer: Encyclopedia of Chemical Technology, Vol. 7, 3d Ed., p. 424 (1979); and U.S. Pat. Nos. 2,453,044; 2,490,866; 3,007,978; 3,544,644; 3,719,718 and 4,048,242.

SUMMARY OF THE INVENTION

Increasing temperature increases the rate of the dicyclopentadiene cracking reaction. At temperatures above 100° C., cyclopentadiene reacts with dicyclopentadiene to form tri, tetra and higher cyclopentadiene polymers. This and other undesirable side reactions are to be avoided if high yields of cyclopentadiene monomer are to be obtained.

This invention provides an improved dicyclopentadiene cracking process which entails rapidly heating the dimer in a heat transfer fluid to the cracking temperature in the absence of the monomer and rapidly removing the cyclopentadiene monomer vapor from the heat transfer fluid prior to condensation to the liquid state. The invention also includes a dicyclopentadiene cracking apparatus or system. Optimum embodiments of the invention provide for about 98–100% conversion of dicyclopentadiene to monomer at about 97–100% purity.

DETAILED DESCRIPTION OF THE INVENTION

In general, the process embodiment of the invention includes introducing dicyclopentadiene in the liquid state into an agitated heat transfer medium maintained at a temperature effective to convert dicyclopentadiene to cyclopentadiene monomer. The dicyclopentadiene is introduced at a point sufficiently below the surface thereof to insure substantially complete conversion to monomeric cyclopentadiene vapor within the heat transfer fluid. The heat transfer fluid is agitated to achieve efficient monomeric cracking and escape of the cyclopentadiene monomer vapor from the heat transfer fluid surface.

The dicyclopentadiene is preheated for conversion from the normal solid state at room temperature to the liquid state prior to introduction below the surface of the heat transfer fluid. The dicyclopentadiene may be preheated to a temperature from about 32° C. to about 170° C., preferably from about 42° C. to about 150° C.

Any inert heat transfer fluid boiling above the cracking temperature of dicyclopentadiene may be utilized. Suitable heat transfer fluids include molten diphenylether, molten diphenylmethane, molten decalin, molten tetralin, and Dowtherm™. The heat transfer fluid is appropriately maintained at a temperature of from about 230° C. to about 350° C., preferably from about 230° C. to about 260° C.

Figure 1:
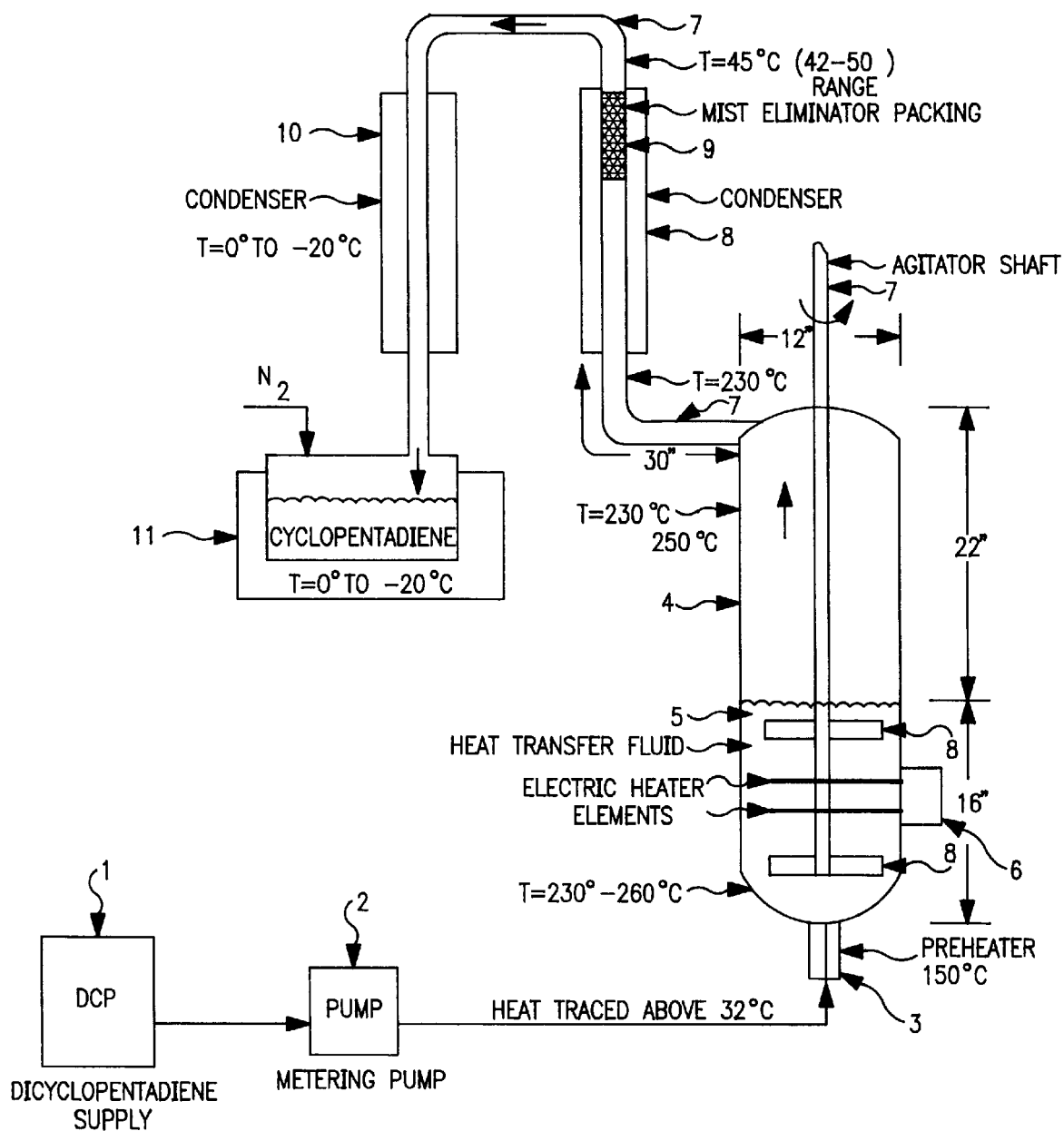
FIG. 1 depicts the dicyclopentadiene system of the invention. Some details of the method are set forth on the figure.
Figure 1:
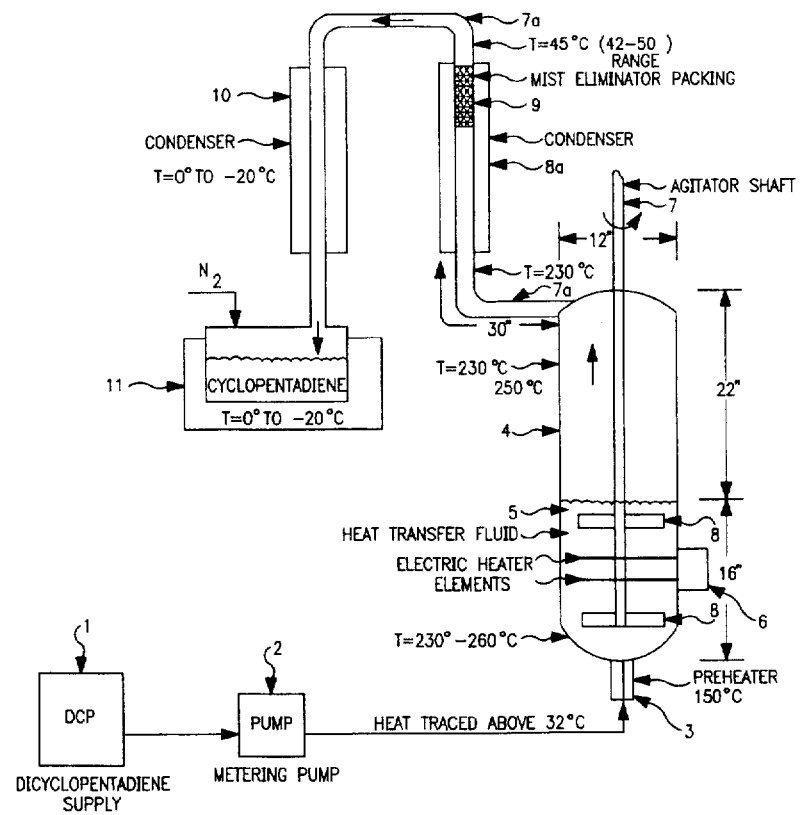

As specifically illustrated by FIG. 1, dicyclopentadiene is transferred from supply 1 by metering pump 2 at a temperature above 50° C. into a preheater 3. In the system of the invention, the preheater is optional. Any means for providing cyclopentadiene in the liquid state may be used. As shown in FIG. 1, the preheater processes dicyclopentadiene at a temperature of about 150° C., which is then passed into a reactor 4 containing a heat transfer fluid 5, such as molten diphenylether, diphenylmethane, decalin, tetralin or Dowtherm™, maintained at a temperature of about 230° C. to 260° C. by electric heater elements 6. The heat transfer fluid is agitated by rotation of the agitator shaft 7, which is provided with blades 8.

The monomeric cyclopentadiene is removed from the reactor 4 at a temperature of about 230° C. to 250° C. through the conduit 7 which is provided with a first condensor 8 and with a mist eliminator packing 9 positioned near the top of the first condensor. The temperature of the condensate which exits from the condenser is about 45° C. The condensate passes through a second condensor 10, maintained at a temperature of about 0° C. to about 20° C., and thence into a chilled receiver 11, where it is maintained at 0° C. to 20° C. under an inert, e.g., nitrogen atmosphere.

In an actual experiment conducted under the conditions described and illustrated by FIG. 1, 1600 pounds of 97% pure dicyclopentadiene was pumped into the reactor—which contained about 7 gallons of molten diphenylether. Approximately 1568 pounds of 99% cyclopentadiene monomer was received in the chilled receiver.

After completion of the cracking reaction, the volume of the heat transfer fluid was still 7 gallons and its viscosity at 35° C. was about the same as that of fresh diphenylether, thus indicating negligible formation of high cyclopentadiene polymers during the cracking reaction.

What is claimed is:

1. In a method for cracking dicyclopentadiene to produce cyclopentadiene monomer, wherein molten dicyclopentadiene is combined with a body of heat transfer fluid maintained within a reaction vessel at a temperature effective to convert dicyclopentadiene to cyclopentadiene monomer vapor, the improvement which comprises:

(i) agitating said body of heat transfer fluid maintained in said reaction vessel;

(ii) introducing monomer and heat transfer fluid free molten dicyclopentadiene into said agitated body of heat transfer fluid, wherein said introduction is made sufficiently below the surface of said heat transfer fluid to provide substantially complete conversion of said introduced dicyclopentadiene to cyclopentadiene monomer vapor, and wherein said agitation of said body of heat transfer fluid facilitates said substantially complete conversion and the escape of said monomer vapor from the surface of said agitated body of heat transfer fluid;

(iii) rapidly removing said monomeric cyclopentadiene vapor from the surface of said agitated body of heat transfer fluid; and (iv) directly condensing said removed monomeric cyclopentadiene vapor to provide liquid cyclopentadiene monomer wherein 98% to 100% of said molten dicyclopentadiene introduced into said agitated body of heat transfer fluid in step (ii) is converted into liquid cyclopentadiene monomer of 97% to 100% purity in step (iv), and wherein negligible formation of high cyclopentadiene polymers occurs in said reaction vessel.

2. The claim 1 method wherein said body of heat transfer fluid is maintained within said reaction vessel at a temperature from about 230° C. to about 350° C.

3. The claim 1 or claim 2 method, wherein said heat transfer fluid is diphenyl ether, diphenyl methane, decalin or tetralin.

* * * * *

UNITED STATES PATENT AND TRADEMARK OFFICE
CERTIFICATE OF CORRECTION

PATENT NO. : 5,877,366
DATED : March 2, 1999
INVENTOR(S) : John M. Birmingham It is certified that error appears in the above-identified patent and that said Letters Patent is hereby corrected as shown below:

IN THE SPECIFICATION

Col. 2, line 27, delete "7" and insert --7a--.

Col. 2, line 28, delete "8" and insert --8a--.

IN THE DRAWINGS

New Figure 1.

Signed and Sealed this

Eighth Day of May, 2001

Attest:

NICHOLAS P. GODICI

Attesting Officer

Acting Director of the United States Patent and Trademark Office